US009936924B2

(12) United States Patent
Stayman et al.

(10) Patent No.: US 9,936,924 B2
(45) Date of Patent: Apr. 10, 2018

(54) TASK-BASED SOURCE-DETECTOR TRAJECTORIES FOR TOMOGRAPHIC IMAGING

(71) Applicant: THE JOHNS HOPKINS UNIVERSITY, Baltimore, MD (US)

(72) Inventors: Joseph Webster Stayman, Baltimore, MD (US); Jeffrey H. Siewerdsen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 163 days.

(21) Appl. No.: 14/780,014

(22) PCT Filed: Mar. 26, 2014

(86) PCT No.: PCT/US2014/031846
§ 371 (c)(1),
(2) Date: Sep. 25, 2015

(87) PCT Pub. No.: WO2014/160766
PCT Pub. Date: Oct. 2, 2014

(65) Prior Publication Data
US 2016/0029978 A1 Feb. 4, 2016

Related U.S. Application Data

(60) Provisional application No. 61/805,247, filed on Mar. 26, 2013.

(51) Int. Cl.
*G06K 9/00* (2006.01)
*A61B 6/03* (2006.01)
(Continued)

(52) U.S. Cl.
CPC ............ *A61B 6/032* (2013.01); *A61B 6/4085* (2013.01); *A61B 6/4441* (2013.01);
(Continued)

(58) Field of Classification Search
CPC ................ G06T 11/006; G06T 11/005; G06T 2211/424; G06T 2211/436;
(Continued)

(56) References Cited

U.S. PATENT DOCUMENTS 7,016,453 B2 3/2006 Ruimi
7,369,695 B2 5/2008 Zettel et al.
(Continued)

FOREIGN PATENT DOCUMENTS

WO 2012-129566 A2 9/2012

OTHER PUBLICATIONS

Prakash et al., Task-based modeling and optimization of a cone-beam CT scanner for musculoskeletal imaging, Oct. 2011, Med. Phys. 38 (10), pp. 5612-5629, applicant cited prior art.*
(Continued)

*Primary Examiner* — Vu Le
*Assistant Examiner* — Guillermo Rivera-Martinez
(74) *Attorney, Agent, or Firm* — Johns Hopkins Technology Ventures

(57) ABSTRACT

An embodiment in accordance with the present invention provides a method for applying task-based performance predictors (measures of noise, spatial resolution, and detectability index) based on numerical observer models and approximations to the local noise and spatial resolution properties of the CBCT reconstruction process (e.g., penalized-likelihood iterative reconstruction). These predictions are then used to identify projections views (i.e., points that will constitute the scan trajectory) that maximize task performance, beginning with the projection view that maximizes detectability, proceeding to the next-best view, and continuing in an (arbitrarily constrained) orbit that can be physically realized on advanced robotic C-arm platforms. The performance of CBCT reconstructions arising from a
(Continued)

task-based trajectory is superior to simple and complex orbits by virtue of improved spatial resolution and noise characteristics (relative to the specified imaging task) associated with the projection views constituting the customized scan orbit.

20 Claims, 4 Drawing Sheets

(51) Int. Cl.
```
A61B 6/00    (2006.01)
G06T 11/00   (2006.01)
G06T 7/00    (2017.01)
G06T 15/08   (2011.01)
G06T 7/30    (2017.01)
A61B 6/12    (2006.01)
```

(52) U.S. Cl.
CPC ............ *A61B 6/5258* (2013.01); *A61B 6/547* (2013.01); *G06T 7/0012* (2013.01); *G06T 7/30* (2017.01); *G06T 11/005* (2013.01); *G06T 15/08* (2013.01); *A61B 6/12* (2013.01); *A61B 6/485* (2013.01); *G06T 2200/04* (2013.01); *G06T 2207/10081* (2013.01); *G06T 2207/10116* (2013.01); *G06T 2207/30064* (2013.01); *G06T 2207/30196* (2013.01); *G06T 2211/421* (2013.01)

(58) Field of Classification Search
CPC ..... G06T 2207/10081; G06T 2211/421; G06T 2207/10116; G06T 7/0012; G06T 2200/04; G06T 2207/10072; G06T 2207/30004; G06T 2210/41; G06T 2207/20182

See application file for complete search history.

(56) References Cited

U.S. PATENT DOCUMENTS

| | | | |
|---|---|---|---|
| 7,853,305 B2 | 12/2010 | Simon et al. | |
| 2005/0117708 A1* | 6/2005 | Cho | A61B 6/547 378/164 |
| 2006/0247513 A1 | 11/2006 | Wang et al. | |
| 2008/0180580 A1* | 7/2008 | Kadrmas | G06T 11/003 348/744 |
| 2008/0242971 A1 | 10/2008 | Klingenbeck-Regn | |
| 2009/0161932 A1* | 6/2009 | Chen | G06T 11/006 382/131 |
| 2009/0225932 A1* | 9/2009 | Zhu | A61B 6/032 378/7 |
| 2010/0121183 A1* | 5/2010 | Taguchi | A61B 6/5264 600/427 |
| 2012/0263360 A1 | 10/2012 | Zhu et al. | |
| 2013/0343673 A1* | 12/2013 | Pal | G06T 11/003 382/298 |
| 2014/0270439 A1* | 9/2014 | Chen | G06T 11/006 382/131 |
| 2015/0187052 A1* | 7/2015 | Amroabadi | A61B 6/5205 382/131 |
| 2015/0216498 A1* | 8/2015 | Schulze | A61B 6/4085 378/19 |

OTHER PUBLICATIONS

Stayman et al., Likelihood-based CT reconstruction of objects containing known components, 2011, 11th International Meeting on Fully Three-Dimensional Image Reconstruction in Radiology and Nuclear Medicine Proceedings, Germany, pp. 254-257.*
Miracle et al., Conebeam CT of the head and neck, part 1: physical principles, 2009, AJNR Am J Neuroradiol 30, pp. 1088-1095.*
Anthoine et al., Some proximal methods for CBCT and PET tomography, 2011, Proc. of SPIE vol. 8138, pp. 81381E-1-12.*
Bian, J., et al., "Evaluation of sparse-view reconstruction from flat-panel-detector cone-beam CT" Phys. Med. Biol. 55 (2010) 6575-6599.
Erdogan, H., et al., "Ordered subsets algorithms for transmission tomography" Phys. Med. Biol. 44 (1999) 2835-2851.
Fessler, J., et al., "Spatial Resolution Properties of Penalized-Likelihood Image Reconstruction: Space-Invariant Tomographs" IEEE Trans Image Process, vol. 5, pp. 1346-1358, (1996).
Gang, G., et al., "Analysis of Fourier-domain task-based detectability index in tomosynthesis and cone-beam CT in relation to human observer performance" Med. Phys. vol. 38, No. 4 (2011).
Gang, G., et al., "Modeling and Control of Nonstationary Noise Characteristics in Filtered-Backprojection and Penalized Likelihood Image Reconstruction" SPIE Medical Imaging, Orlando (2013).
Prakash, P., et al., "Task-based modeling and optimization of a cone-beam CT scanner for musculoskeletal imaging" Med. Phys. 38(10): 5612-5630 (2011).
Richare, S., "Comparison of model and human observer performance for detection and discrimination tasks using dual-energy x-ray images" Med. Phys. 35(11): 5043-5053 (2008).
Sidky, E., et al., "Sampling conditions for gradient-magnitude sparsity based image reconstruction algorithms" Medical Imaging: Physics of Medical Imaging, vol. 8313 (2012).
Siewerdsen, J., et al., "Optimization of x-ray imaging geometry (with specific application to flat-panel cone-beam computed tomography)" Med. Phys. 27(8) 1903-1914 (2000).
Siewerdsen, J., et al., "A framework for noise-power spectrum analysis of multidimensional images" Med. Phys. 29 (11): 2655-2671 (2002).
Stayman, J., et al., "Efficient Calculation of Resolution and Covariance for Penalized-Likelihood Reconstruction in Fully 3-D SPECT" IEEE Transactions on Medical Imaging, vol. 23, No. 12, Dec. 2004.
Thibault, J., et al., "A three-dimensional statistical approach to improved image quality for multislice helical CT" Med Phys, vol. 34, pp. 4526-4544 (2007).
Tward, D., et al., "Noise aliasing and the 3D NEQ of flat-panel cone-beam CT: Effect of 2D/3D apertures and sampling" Med. Phys. 36(8): 3830-3843 (2009).
Wagner, R., et al., "Application of information theory to the assessment of computed tomography" Medical Physics, vol. 6, pp. 83-94 (1979).
Zheng, Z., et al., "Identifying Sets of Favorable Projections for Few-View Low-Dose Cone-Beam CT Scanning" 11th Int'l Meeting on Fully 3D Image Reconstruction in Radiology and Nuclear Medicine, Potsdam, Germany (2011) pp. 314-317.

* cited by examiner

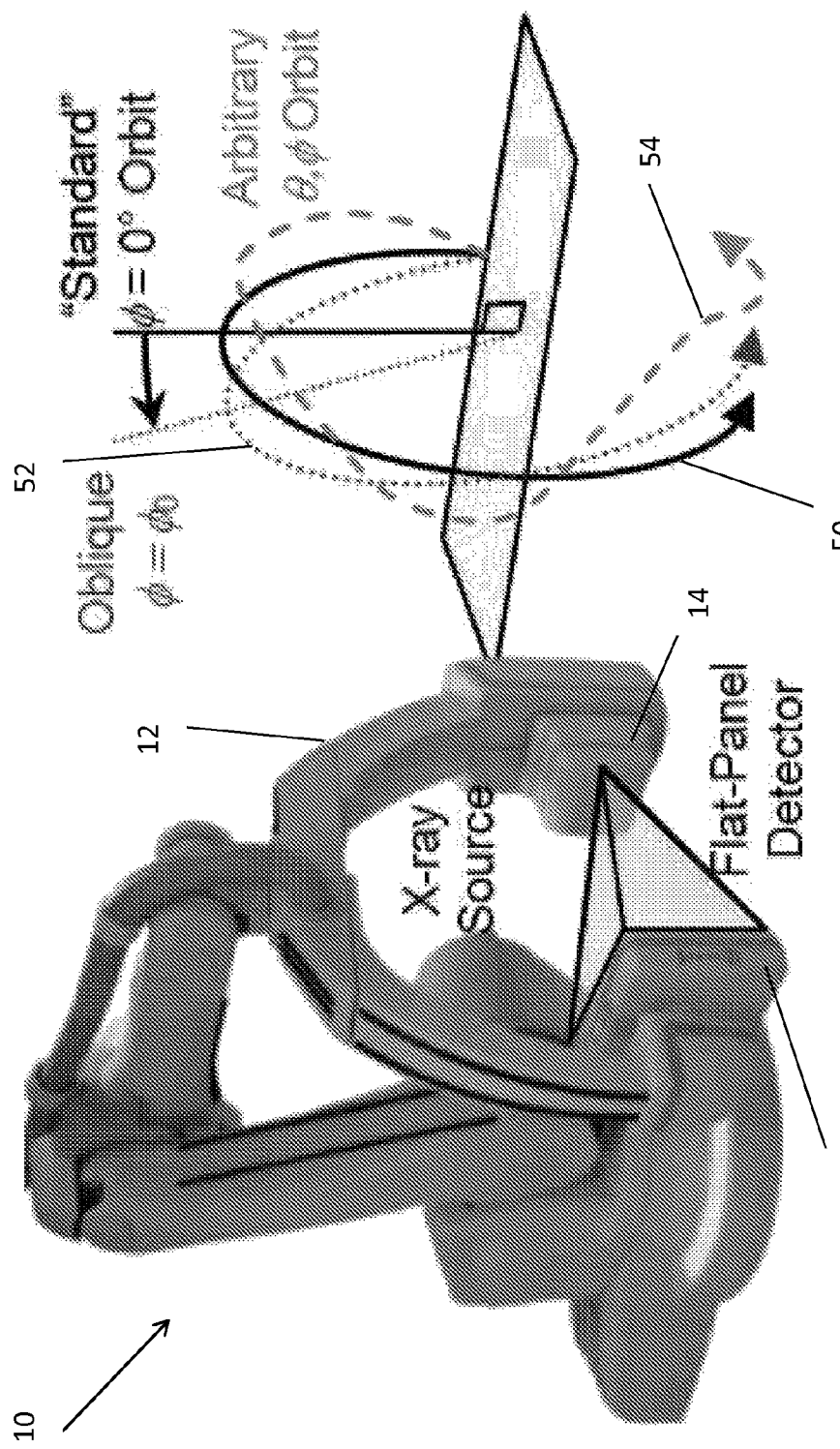

TASK-BASED SOURCE-DETECTOR TRAJECTORIES FOR TOMOGRAPHIC IMAGING

CROSS-REFERENCE TO RELATED APPLICATIONS

This application is a 35 U.S.C. § 371 U.S. national entry of International Application PCT/US2014/031846, having an international filing date of Mar. 26, 2014, which claims the benefit of U.S. Provisional Application No. 61/805,247, filed Mar. 26, 2013, the content of each of the aforementioned applications is herein incorporated by reference in their entirety.

GOVERNMENT SUPPORT

This invention was made with government support under CA112163 and EB014964, both awarded by the National Institutes of Health. The government has certain rights in the invention.

FIELD OF THE INVENTION

The present invention relates generally to imaging. More particularly the present invention relates to a system and method for task-based source detected trajectories for tomographic imaging.

BACKGROUND OF THE INVENTION

Traditional cone-beam CT interventional systems are largely "un-informed" with respect to the properties of the patient (i.e., anatomical context surrounding a given region or structure of interest) or the imaging task that needs to be conducted. Rudimentary exceptions are simple specification of the patient in generic terms of body habitus (e.g., small or large) and a generic description of task in terms of desirable image characteristics (e.g., smooth or sharp). The conventional paradigm makes no account of patient-specific characteristics or more quantitative specification of the spatial resolution, noise, and imaging task in defining the source detector scan orbit. Instead, the scan orbit is almost always entirely "prescriptive"—e.g., a circular orbit in a plane convenient for the mechanical characteristics of the scanner. As such, positioning of the interventional system (e.g., a needle or other interventional device), positioning of the source-detector throughout data acquisition (i.e. the orbital trajectory), and other acquisition parameters are conventionally selected based on coarse heuristics of body size, target location, and x-ray technique charts that typically (in a population sense) produce "good" image results.

It would therefore be advantageous to provide a system and method for creating task-based and/or patient-specific trajectories for interventional imaging.

SUMMARY OF THE INVENTION

The foregoing needs are met, to a great extent, by the present invention, wherein in one aspect a method of obtaining an interventional cone-beam computed tomography (CBCT) image of a subject includes identifying performance predictors that affect the quality of an image. The method includes applying the performance predictors that affect the quality of the image to properties of a reconstruction of the image. The method also includes identifying projection views to maximize task performance. The identifying begins with a projection view that maximizes detectability, proceeding to a next-best view, and continuing in an orbit of a C-arm of an imaging machine. Additionally, the method includes initiating a CBCT scan of the subject following the identified projection views to generate the image.

In accordance with an aspect of the present invention, the method includes using the task-based performance predictors that take the form of at least one of a group consisting of measures of noise, spatial resolution, and detectability index. The method includes using the task-based performance predictors based on numerical observer models and approximations to the properties of the reconstruction. The method also includes using the properties of the reconstruction that take the form of at least one from a group consisting of local noise and spatial resolution and using a penalized-likelihood iterative reconstruction. Additionally, the method includes arbitrarily constraining the orbit. The method includes determining the performance predictors of an image using a general vectorized forward model:

$$\bar{y}=D\{b\}\exp(-A\mu),$$

and using a system matrix for an entire orbit comprising, $$A(\{\theta_1, \phi_1\}, \ldots, \{\theta_N, \phi_N\}) = [A_{\theta_1,\phi_1}^T \ A_{\theta_2,\phi_2}^T \ \ldots \ A_{\theta_N,\phi_N}^T]^T.$$

The method also includes using the penalized-likelihood iterative reconstruction with an estimator defined as:

$$\hat{\mu}=\arg\max_\mu L(\mu;y)-\beta R(\mu),$$

The method further includes registering the imaging machine.

In accordance with another aspect of the present invention, a non-transitory computer readable medium is programmed with a method of obtaining an image of a subject with a C-arm CT scanning imaging machine including determining task-based performance predictors. The method programmed on the non-transitory computer readable medium also includes applying the task-based performance predictors to aspects of a scanning reconstruction process. Additionally, the method includes identifying points that will constitute a scan trajectory of a C-arm CT scanning platform. The points are identified using application of the task-based performance predictors to aspects of the scanning reconstruction process. The method also includes generating an optimized image of the subject using the scan trajectory.

In accordance with yet another aspect of the present invention the method includes using data from previous scans of the subject in order to determine the task-based performance predictors and using task-based performance predictors that take the form of at least one of a group consisting of measures of noise, spatial resolution, and detectability index. The method includes using task-based performance predictors based on numerical observer models and approximations to the properties of the reconstruction. The method also includes applying the task-based performance predictors to at least one of a group consisting of local noise and spatial resolution. Additionally, the method includes applying a penalized-likelihood iterative reconstruction to the scanning reconstruction process. The scan trajectory can be constrained arbitrarily. The task-based performance predictors of an image can be determined using a general vectorized forward model:

$$\bar{y}=D\{b\}\exp(-A\mu),$$

Also, system matrix for an entire orbit can take the form of, $$A(\{\theta_1, \phi_1\}, \ldots, \{\theta_N, \phi_N\}) = [A_{\theta_1,\phi_1}^T \; A_{\theta_2,\phi_2}^T \; \ldots \; A_{\theta_N,\phi_N}^T]^T.$$

The imaging machine can also be registered.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 1A illustrates a schematic view of an exemplary robotically controlled C-arm that could be used to execute the method of the present invention.

FIG. 1B illustrates a schematic view of several orbits for a C-arm according to FIG. 1A.

DETAILED DESCRIPTION

Figures 2A, 2B, 2C:
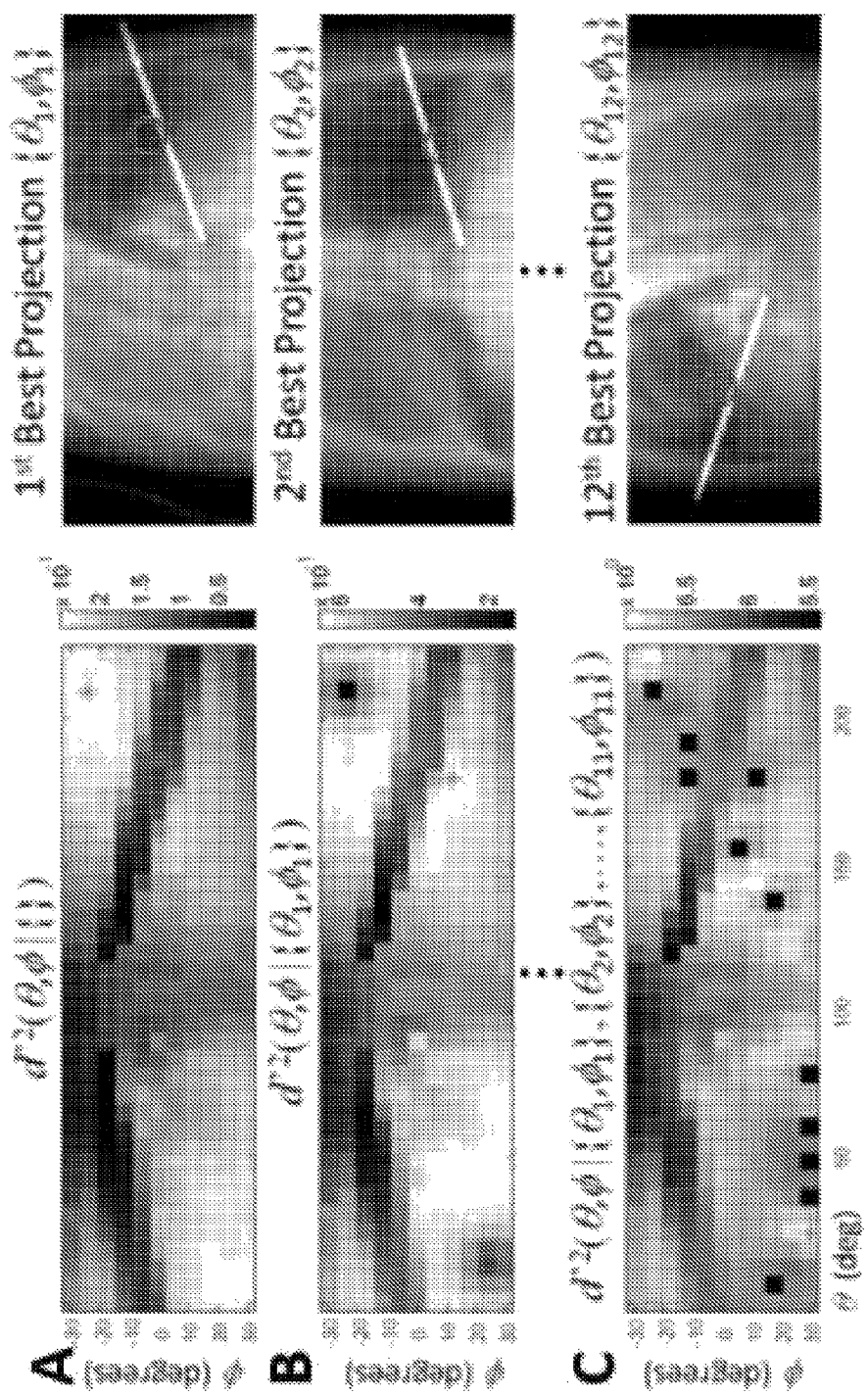
FIGS. 2A-2C illustrate exemplary images from a simulated thoracic interventional imaging scenario.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a method for applying task-based performance predictors (measures of noise, spatial resolution, and detectability index) based on numerical observer models and approximations to the local noise and spatial resolution properties of the CBCT reconstruction process (e.g., penalized-likelihood iterative reconstruction). These predictions are then used to identify projections views (i.e., points that will constitute the scan trajectory) that maximize task-based performance, beginning with the projection view that maximizes detectability, proceeding to the next-best view, and continuing in an (arbitrarily constrained) orbit that can be physically realized on advanced robotic C-arm platforms.

The performance of CBCT reconstructions arising from a task-based trajectory is superior to simple and complex orbits by virtue of improved spatial resolution and noise characteristics (relative to the specified imaging task) associated with the projection views constituting the customized scan orbit.

The present invention leverages the great amount of patient and procedure-specific prior knowledge (e.g., prior scans from diagnosis and planning, and specific imaging tasks like detection and localization) that are commonly available in interventional imaging scenarios to design customized data acquisition trajectories. These trajectories are designed to maximize task specific performance allowing for possible reductions in radiation dose (fewer projections or lower exposure), improved image quality (and specifically, image quality optimized for the imaging task), and enhancements to the interventional workflow (e.g., faster, automatic positioning, avoidance of repeat scans). For instance, FIG. 1A illustrates a schematic view of an exemplary scanner with a robotically controlled C-arm that could be used to execute the method of the present invention. Such a robotically controlled C-arm is capable of a wide range of source detector positions. In the scanner 10 illustrated in FIG. 1A, a robotically controlled C-arm 12 includes an x-ray source 14 is disposed opposite a flat-panel detector 16. The x-ray source 14 and the flat-panel detector 16 are coupled to the C-arm such that they can be moved through a variety of positions, traditional, and non-traditional orbits. Traditional cone-beam CT acquisitions are typically acquired over a standard 180°+ fan angle orbit with no inclination. However, robotically controlled C-arms allow for oblique orbits or arbitrarily complex variations in rotation angle (θ) and obliquity (φ) throughout the orbit. FIG. 1B illustrates a schematic diagram of exemplary orbits of a robotically controlled C-arm. As illustrated in FIG. 1B, the solid line 50 shows a standard θ=0° orbit. Dotted line 52 illustrates an oblique orbit φ=φ$_0$, and dashed line 54 illustrates an arbitrary or complex orbit with variations in rotation angle ((θ) and obliquity (φ) throughout the orbit.

Both iterative reconstruction and performance predictors require a system model that must be general enough to accommodate particular acquisition geometries and include measurement noise to leverage the advantages of statistical approaches. The present invention therefore uses the following general vectorized forward model for the mean measurements:

$$\bar{y} = D\{b\}\exp(-A\mu), \tag{1}$$

where the measurement vector, y, is related to the volume μ through Beer's Law and includes measurement-dependent gains in the diagonal matrix D{b}. Each element of the system matrix, A, models the contribution of a specific voxel to a specific projection measurement. This model can accommodate arbitrary geometries like those obtainable with robotic C-arms, such as the exemplary system illustrated in FIGS. 1A and 1B. The system matrix for an entire orbit is comprised of smaller matrices for each 2D projection:

$$A(\{\theta_1, \phi_1\}, \ldots, \{\theta_N, \phi_N\}) = [A_{\theta_1,\phi_1}^T \; A_{\theta_2,\phi_2}^T \; \ldots \; A_{\theta_N,\phi_N}^T]^T. \tag{2}$$

The present invention focuses on a system orbit parameterized by two angles, rotation angle (θ) and obliquity angle (φ). However, it should be noted that while the two angle scenario is described in further detail herein, robotic C-arms are capable of translations and modifications of the source-detector distance yielding many more possibilities.

Once a specific forward model and trajectory has been chosen, a penalized-likelihood estimation approach is used for reconstruction. Unlike many analytic approaches, arbitrary trajectories and data sparsity are handled inherently, without modification of weighting factors, etc., once A has been defined. The following estimator can be used:

$$\hat{\mu} = \arg \max_\mu L(\mu; y) - \beta R(\mu), \quad (3)$$

which adopts a Poisson log-likelihood, L, and a quadratic penalty, $R(\mu) = \mu^T R \mu$. A separable paraboloidal surrogates approach, known to those of skill in the art, is applied to iteratively solve EQ. (3).

The estimator in EQ. (3) is convenient, because one may write approximate predictors for the local point spread function (PSF) and local covariance, or equivalently, the local modulation transfer function (MTF) and local noise-power spectrum (NPS). Such imaging performance metrics are prevalent in image quality assessment and are leveraged here directly toward the 3D image acquisition and reconstruction process. As known to one of skill in the art, local PSF and covariance are approximately:

$$PSF_j \approx [A^T DA + \beta R]^{-1} A^T DA e_j$$

$$Cov\{\hat{\mu}_j\} \approx [A^T DA + \beta R]^{-1} A^T DA [A^T DA + \beta R]^{-1} e_j \quad (4)$$

where $D = D\{y\}$ and $e_j$ denotes a vector with unity $j^{th}$ element and zero otherwise (specifying the location of interest as with a Kronecker delta function). Note that object-dependence enters EQ. (4) through D, which is dependent on the measurements. Ordinarily, this would be a problem (e.g. you cannot design a trajectory to acquire measurements based on measurements that have not yet been acquired. However, one can use a previously acquired CT volume to generate synthetic measurements for the prediction process. Such prior image could be obtained from a number of sources, including, but not limited to, preoperative CT, an initial intraoperative CBCT, anatomical atlases, etc. While EQ. (4) can be computed precisely using iterative approaches, such methods have high computational burden. Alternately, one may use a Fourier approximation to EQ. (4):

$$MTF_j \approx \frac{\mathcal{F}\{A^T DA e_j\}}{\mathcal{F}\{A^T DA e_j + \beta R e_j\}}$$

$$NPS_j \approx \frac{\mathcal{F}\{A^T DA e_j\}}{|\mathcal{F}\{A^T DA e_j + \beta R e_j\}|^2}, \quad (5)$$

where F denotes a discrete Fourier transform and the divisions are element-by-element. With expressions for local MTF and NPS, one may predict estimator performance using a model observer. For example, using a non-prewhitening matched-filter observer one can express the detectability index as $$d'^2 = \frac{\left[ \iiint (MTF_j \cdot W_{Task})^2 df_x df_y df_z \right]^2}{\iiint NPS_j \cdot (MTF_j \cdot W_{Task})^2 df_x df_y df_z}, \quad (6)$$

where $W_{Task}$ is the so-called task function given by the Fourier transform of the difference of two hypotheses (e.g., signal absent vs. signal present). Many other choices of numerical observer known to or conceivable by one of skill in the art are possible, including those that more closely model the human visual system. However, the current initial investigations employ this simple model, which has demonstrated reasonable agreement with human observers in tomographic imaging relative to simple imaging tasks. Thus, using EQ. (6), one may then predict performance for a given task ($W_{Task}$), object (via D in EQ. (5)), location (subscript j), and acquisition trajectory (A in EQ. (5)).

Because the present invention is directed to finding the best source-detector trajectory for a given task and patient in an interventional setting where anatomical information is available from preoperative CT (or prior CBCT), EQ. (6) is optimized over A. Recalling EQ. (2), $A = A(\{\theta_1, \varphi_1\}, \ldots, \{\theta_N, \varphi_N\})$ can be substituted for different sets of projections into EQ. (6) to obtain $d'2(\{\theta_1, \varphi_1\}, \ldots, \{\theta N, \varphi N\})$.

The general optimization task is difficult, and performing a search over all possible combinations of N angles is prohibitive for larger N. Therefore, the following notation is used:

$$d'^2(\theta, \varphi | \{\theta_1, \varphi_1\}, \ldots, \{\theta_N, \varphi_N\}), \quad (7)$$

which denotes a 2D function over $\theta$ and $\varphi$ that expresses the overall detectability that a given projection angle yields when added to an orbit already containing a specified set of N projections. In other words, EQ. (7) yields a function whose maximum identifies the "next best projection view" based on task detectability. Thus, highly performing sets of projections can be found via a greedy approach where new angles are added to a growing set of projection angles starting with an empty set. That is, a set of projection angles is then constructed by iteratively finding the next most valuable projection $(\theta_{N+1}, \varphi_{N+1})$ in the detectability map and adding it to the existing set of N angle pairs. Stopping criteria may be formed based on number of angles, dose allocation, acquisition time, detectability, etc.

This greedy optimization approach is illustrated in FIGS. 2A-2C for a simulated thoracic interventional imaging scenario. In this example, the patient anatomy contains a high-density surgical tool that is part of the intervention, as well as a low-contrast pulmonary spherical nodule in a collapsed lung that is difficult to identify in projection images. The task function is the Fourier transform of the spherical nodule, and the location j is matched to the true location of the nodule. Detectability is computed over a limited −30° to 30° obliquity and a 220° rotational range (samples every 6° in each direction); however, these limits may be adjusted to accommodate the mechanical capabilities and constraints for particular devices and interventional scenarios.

EXAMPLE

An exemplary implementation of the present invention is described herein, in order to further illustrate the present invention. The exemplary implementation is included merely as an example and is not meant to be considered limiting. Any implementation of the present invention on any suitable subject known to or conceivable by one of skill in the art could also be used, and is considered within the scope of this application.

This example builds on the thoracic intervention scenario discussed in the previous section to illustrate the results of the proposed task-based trajectory design approach. In this investigation, a system with 1200 mm source-detector distance, 600 mm source-axis distance, and a 300×800 detector with 0.776 mm pixel pitch was simulated. A 3003 volume (1 mm voxels) was used for all experiments, and an exposure equivalent of 103 photons per detector element was used for Poisson noise generation.

Figures 3A, 3B, 3C, 3D, 3E:
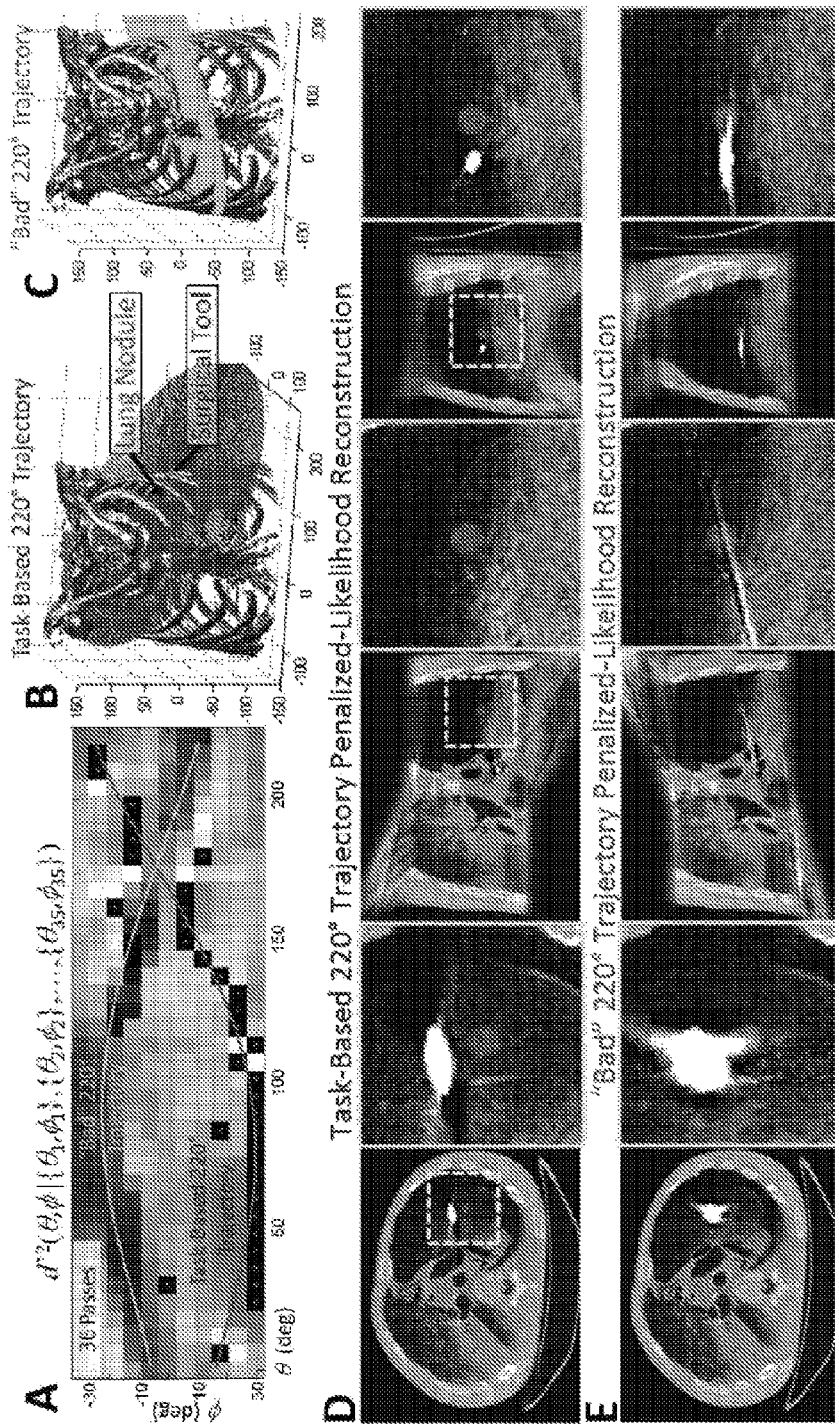
FIG. 3A illustrates a final detectability map and selected angle pairs.
FIGS. 3B and 3C illustrate two exemplary orbits of the C-arm relative to the bony anatomy, lung nodule, and surgical tool.
FIGS. 3D and 3E illustrate penalized-likelihood reconstructions associated with each trajectory.

For these studies, it was assumed that the image volume is known and perfectly registered for orbital trajectory design. To design a custom orbit for the spherical lung nodule detection task, 36 passes of the optimization approach detailed in the previous section were conducted. The final detectability map and selected angle pairs are illustrated in FIG. 3A. Note that the selected projection angles tend to avoid overlap of the high-density surgical tool and the low-contrast nodule in projections. The influence of the surgical tool is apparent in the upper dark arc in the detectability map. Similarly, while lateral views are discouraged early in the optimization (dark vertical band in FIGS. 2A-2C), these views become important in later iterations (in FIG. 3A this dark band is absent).

Despite the lack of a constraint for a continuous trajectory, the task-based design has produced largely contiguous projection angle pairs. To produce a completely continuous orbit, a polynomial curve fit through the 36 selected positions was performed to produce a 220° orbit with 1° steps. A second "bad" orbit was also designed via a curve fit through regions of minimum detectability for comparison. These two orbits are illustrated in FIGS. 3B and 3C relative to the bony anatomy, lung nodule, and surgical tool. Note that while the task-based orbit avoids projections of the lung nodule that overlap with the surgical tool and bone, the "bad" trajectory is that in which the nodule and tool overlap in nearly every view.

The penalized-likelihood reconstructions associated with each trajectory are shown in FIGS. 3D and 3E. The low-contrast pulmonary nodule has qualitatively better detectability in the designed orbit, while the "bad" trajectory results in significantly increased blur and noise due to the low-fidelity data associated with projections through the high-density surgical tool. These effects are most pronounced in the axial images; however, significant streaking and noise is also apparent in the "bad" orbit in the sagittal and coronal slices.

A second experiment using the task-based trajectory design was conducted for a second task function. All simulation settings except for exposure (here set to 105 photons per detector element) remain the same as in the previous experiment. In this scenario, a task function was selected based on a binary hypothesis test consisting of the same spherical nodule shifted 1 mm laterally in the patient, emulating a lateral localization task that is very different from the nodule detection task in the first experiment and emphasizing higher spatial frequencies in maximizing the detectability index.

Figures 4A, 4B, 4C:
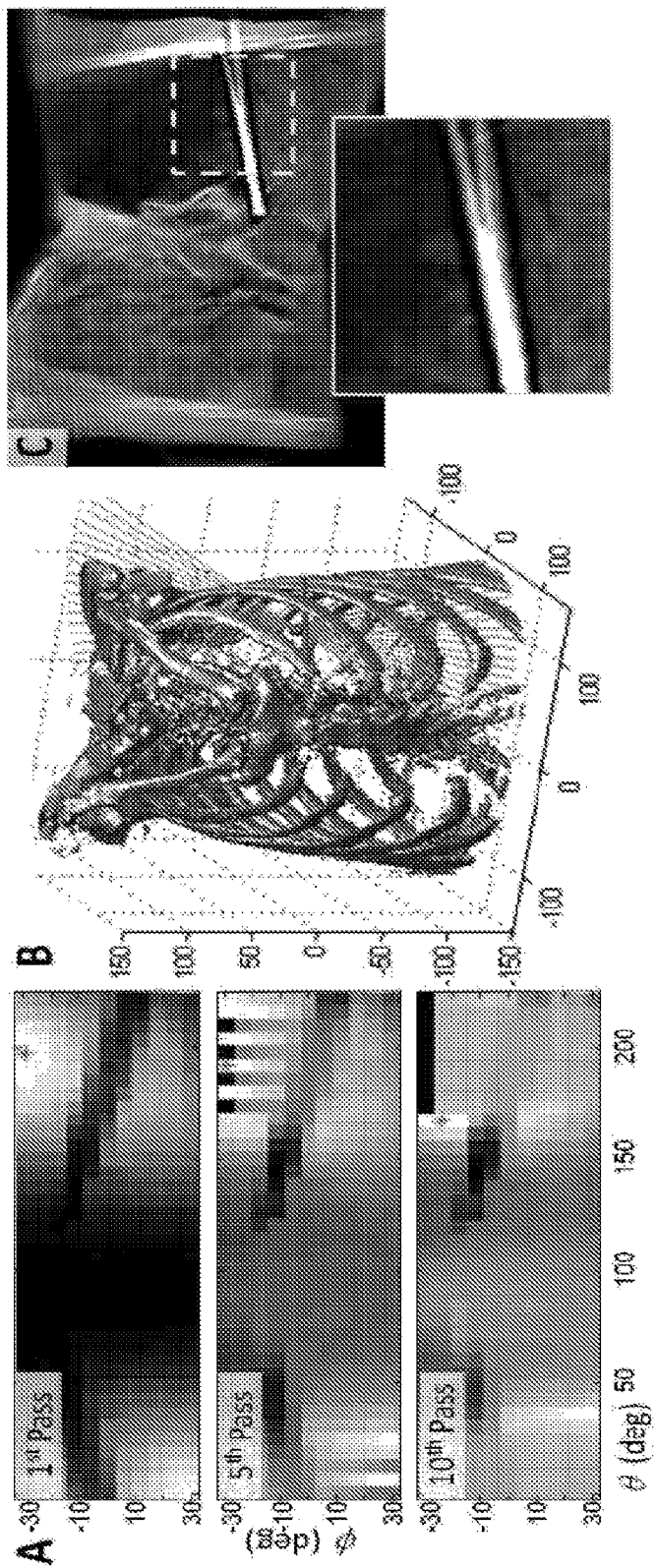
FIGS. 4A-4C illustrate results of the lateral localization task.

The results of the lateral localization task are summarized in FIGS. 4A-4C. FIG. 4A shows the detectability maps for the 1st, 5th, and 10th passes of the trajectory design. The maps reveal a number of interesting features. Not surprisingly, lateral projections contribute little to task performance for the lateral localization task (particularly in early iterations), and AP/PA views with high obliquities that separate the surgical tool and the low-contrast nodule are preferred. In addition, the initial angular pairs are spaced at intervals before filling in later iterations. A trajectory using a 3° sampling interval was fit to the best 10 angle pairs and is illustrated in FIG. 4B. The resulting task-based trajectory for lateral localization is a limited angle acquisition (i.e., tomosynthesis). Coronal slices of a penalized-likelihood reconstruction are shown in FIG. 4C. Even though the acquisition is highly limited in angle with a small number of views, the nodule is easily localized laterally based on this limited-angle reconstruction.

The present invention implements a methodology for designing task-based trajectories for interventional imaging using penalized-likelihood reconstruction. The preliminary results show the potential for increased performance over standard orbits, including conventional circular orbits and (unlucky) oblique orbits that align patient anatomy, interventional tools, and/or the structure of interest in a manner that reduces detectability. There are a number of possible extensions to the proposed methodology including generalizations to more arbitrary geometries (e.g., including translation, magnification, etc.), optimization of detectability over a volume-of-interest instead of a single point, optimization of multiple task functions, limited field-of-view reconstructions, and addition of additional constraints (e.g., radiation dose and acquisition time). Another important challenge is an extension of these concepts to nonquadratic penalty approaches that are commonly used in CT.

One important practical consideration for this invention is that the methodology presumes having a registered preoperative CT for design. Thus, a functional workflow must include a registration step, perhaps based on an initial projection image and 2D-3D registration. Because this registration is likely imperfect, there is also the possibility of an adaptive design technique that adjusts the orbit "on-the-fly." That is, as more information is obtained about the patient volume, the imaging system adapts its trajectory to maximize performance.

The proposed method leverages the wealth of information available in interventional imaging and combines it with methods of task-based performance evaluation to define optimal trajectories. Whereas traditional approaches tend to neglect the wealth of prior knowledge or use it in only a very coarse manner, the proposed framework integrates it fundamentally into the acquisition process. This is an important step in making imaging systems more aware of the objects they are imaging and the imaging tasks for which they intended, leading to increased imaging performance and potential reduction in dose.

It should be noted that the methods of the present invention described above can be implemented with a computing device. The computing device can be hard wired to the imaging machine or can be networked in a wired or wireless manner. The computing device can also communicate with a server or other remote computing device in order to execute these steps. A non-transitory computer readable medium programmed to execute the methods can be loaded on the computing device or in communication with the computing device. The non-transitory computer readable medium can take any suitable form known to one of skill in the art. The non-transitory computer readable medium is understood to be any article of manufacture readable by a computer or other computing device. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. The computing device can take the form of a PC, tablet, smartphone, processor, or any other suitable computing device known to or conceivable by one of skill in the art.

The many features and advantages of the invention are apparent from the detailed specification, and thus, it is intended by the appended claims to cover all such features and advantages of the invention which fall within the true spirit and scope of the invention. For example, while the application focuses on the specific reconstruction technique of penalized-likelihood estimation, the technique of task-specific trajectory design is equally applicable for any other reconstruction methods where noise and resolution predictions are available. Thus, when filtered-backprojection is used, the present invention could be applied to design a trajectory to fit the filtered-backprojection methodology. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of obtaining an interventional cone-beam computed tomography (CBCT) image of a subject comprising:
   identifying task-based performance predictors that affect the quality of an image;
   applying the task-based performance predictors that affect the quality of the image to properties of a reconstruction of the image;
   identifying projection views to maximize task performance, wherein the identifying begins with a projection view that maximizes detectability, proceeding to a next-best view, and continuing in an orbit of a C-arm of an imaging machine, wherein the identified projection views form an arbitrary orbit with variations in rotation angle, θ, and obliquity, φ, throughout the orbit; and
   initiating a CBCT scan of the subject following the identified projection views to generate the image according to the identified and applied task-based performance predictors.

2. The method of claim 1 further comprising using the task-based performance predictors that take the form of at least one of a group consisting of measures of noise, spatial resolution, and detectability index.

3. The method of claim 1 further comprising using the task-based performance predictors based on numerical observer models and approximations to the properties of the reconstruction.

4. The method of claim 1 further comprising using the properties of the reconstruction that take the form of at least one from a group consisting of local noise and spatial resolution.

5. The method of claim 1 further comprising using a penalized-likelihood iterative reconstruction.

6. The method of claim 1 further comprising arbitrarily constraining the orbit.

7. The method of claim 1 further comprising determining the performance predictors of an image using a general vectorized forward model:

$$\bar{y}=D\{b\}\exp(-A\mu),$$

where a measurement vector, y, is related to the volume attentaion, μ, D {b}, is a diagonal matrix, and A is a system matrix of an entire scanning orbit.

8. The method of claim 1 further comprising using a system matrix for an entire orbit comprising, $$A(\{\theta_1, \phi_1\}, \ldots, \{\theta_N, \phi_N\}) = [A_{\theta_1,\phi_1}^T \ A_{\theta_2,\phi_2}^T \ \ldots \ A_{\theta_N,\phi_N}^T]^T.$$

where A is parameterized by a rotation angle, θ, and an obliquity angle, φ, throughout a scanning orbit.

9. The method of claim 5 further comprising using the penalized-likelihood iterative reconstruction with an estimator defined as:

$$\hat{\mu}=\arg\max{}_\mu L(\mu;y)-\beta R(\mu),$$

where L(μ; y) corresponds to a Poisson log-likelihood, L and βR(μ) corresponds to a quadratic penalty.

10. The method of claim 1 further comprising registering the imaging machine.

11. A non-transitory computer readable medium programmed with a method of obtaining an image of a subject with a C-arm CT scanning imaging machine comprising:
    determining task-based performance predictors;
    applying the task-based performance predictors to aspects of a scanning reconstruction process;
    identifying points that will constitute an arbitrary scan trajectory of a C-arm CT scanning platform, wherein the points are identified using application of the task-based performance predictors to aspects of the scanning reconstruction process, wherein the arbitrary scan trajectory includes variations in rotation angle, θ, and obliquity, φ, throughout the orbit; and
    generating an optimized image of the subject using the arbitrary scan trajectory.

12. The non-transitory computer readable medium of claim 11 further comprising using data from previous scans of the subject in order to determine the task-based performance predictors.

13. The non-transitory computer readable medium of claim 11 further comprising using task-based performance predictors that take the form of at least one of a group consisting of measures of noise, spatial resolution, and detectability index.

14. The non-transitory computer readable medium of claim 11 further comprising using task-based performance predictors based on numerical observer models and approximations to the properties of the reconstruction.

15. The non-transitory computer readable medium of claim 11 further comprising applying the task-based performance predictors to at least one of a group consisting of local noise and spatial resolution.

16. The non-transitory computer readable medium of claim 11 further comprising applying a penalized-likelihood iterative reconstruction to the scanning reconstruction process.

17. The non-transitory computer readable medium of claim 11 further comprising constraining the scan trajectory arbitrarily.

18. The non-transitory computer readable medium of claim 11 further comprising determining the task-based performance predictors of an image using a general vectorized forward model:

$$\bar{y}=D\{b\}\exp(-A\mu),$$

where a measurement vector, y, is related to the volume attentaion, μ, D{b}, is a diagonal matrix, and A is a system matrix of an entire scanning orbit.

19. The non-transitory computer readable medium of claim 11 further comprising using a system matrix for an entire orbit comprising, $$A(\{\theta_1, \phi_1\}, \ldots, \{\theta_N, \phi_N\}) = \begin{bmatrix} A_{\theta_1,\phi_1}^T & A_{\theta_2,\phi_2}^T & \ldots & A_{\theta_N,\phi_N}^T \end{bmatrix}^T.$$

where A is parameterized by a rotation angle, θ, and an obliquity angle, φ, throughout a scanning orbit.

20. The non-transitory computer readable medium of claim 11 further comprising registering the imaging machine.

* * * * *